United States Patent
Yeo et al.

(10) Patent No.: US 10,113,964 B2
(45) Date of Patent: Oct. 30, 2018

(54) OPTICAL DETECTION APPARATUS AND METHOD OF COMPENSATING DETECTION ERROR

(71) Applicant: SAMSUNG ELECTRONICS CO., LTD., Suwon-si (KR)

(72) Inventors: Yeong-bae Yeo, Seoul (KR); Hyun-soo Jang, Uiwang-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 464 days.

(21) Appl. No.: 14/513,386

(22) Filed: Oct. 14, 2014

(65) Prior Publication Data

US 2015/0177141 A1 Jun. 25, 2015

Related U.S. Application Data

(60) Provisional application No. 61/977,877, filed on Apr. 10, 2014.

(30) Foreign Application Priority Data

Dec. 24, 2013 (KR) .................... 10-2013-0162577

(51) Int. Cl.
*G01N 21/59* (2006.01)
*G01N 21/75* (2006.01)

(52) U.S. Cl.
CPC ............ *G01N 21/59* (2013.01); *G01N 21/75* (2013.01); *G01N 2201/0612* (2013.01); *G01N 2201/0621* (2013.01); *G01N 2201/0696* (2013.01); *G01N 2201/105* (2013.01); *G01N 2201/121* (2013.01); *G01N 2201/127* (2013.01)

(58) Field of Classification Search
CPC .............................. G01N 21/59; G01N 21/75
See application file for complete search history.

(56) References Cited

U.S. PATENT DOCUMENTS

| | | | | |
|---|---|---|---|---|
| 2003/0020030 A1* | 1/2003 | Harada | ................ | G01N 21/474 250/573 |
| 2005/0186684 A1* | 8/2005 | Woudenberg | ......... | B01L 3/5027 436/174 |
| 2011/0194114 A1* | 8/2011 | Yeo | ........................ | B01L 3/5027 356/435 |
| 2012/0177538 A1* | 7/2012 | Kanayama | ................ | G01J 3/36 422/82.05 |

(Continued)

FOREIGN PATENT DOCUMENTS

JP 2010-256290 A 11/2010

*Primary Examiner* — Krishnan S Menon
*Assistant Examiner* — Dwan A Gerido
(74) *Attorney, Agent, or Firm* — Sughrue Mion, PLLC

(57) ABSTRACT

An optical detection apparatus for measuring detection chambers of a specimen cartridge includes: a light source unit including light sources which are arranged along a scan line on which the detection chambers are aligned to be scanned, and configured to emit light rays to the detection chambers; and an optical detector configured to detect the light rays having passed through corresponding detection chambers disposed on the scan line. The light sources include main wavelength light sources which are used for measuring samples disposed in the detection chambers, and a sub-wavelength light source which is used for correcting a measuring error.

22 Claims, 7 Drawing Sheets

(56) References Cited

U.S. PATENT DOCUMENTS

2012/0308437 A1* 12/2012 Zhou ............... G01N 21/03
　　　　　　　　　　　　　　　　　　　422/82.05
2013/0156642 A1* 6/2013 Lous ............... G01N 21/76
　　　　　　　　　　　　　　　　　　　422/52

* cited by examiner

OPTICAL DETECTION APPARATUS AND METHOD OF COMPENSATING DETECTION ERROR

CROSS-REFERENCE TO RELATED APPLICATIONS

This application claims priority from Korean Patent Application No. 10-2013-0162577, filed on Dec. 24, 2013, in the Korean Intellectual Property Office, and U.S. Provisional Patent Application No. 61/977,877, filed on Apr. 10, 2014, the disclosures of which are incorporated herein in their entireties by reference.

BACKGROUND

1. Field

One or more exemplary embodiments relate to an optical detection apparatus and a method of compensating a detection error, and more particularly, to a scan-type optical detection apparatus and a method of compensating a detection error.

2. Description of the Related Art

Reliance on point-of-care (POC) blood analysis devices using disposable cartridges has been increasing in the medical field, and research and development of small-sized POC blood analysis devices enabling quick and accurate blood tests have been performed. For instance, in a lab-on-a-chip based blood analyzer for field tests, miniaturization, weight reduction, and support of simultaneous inspection of multiple items are important factors. Accordingly, a lab-on-a-chip (LOC) specimen cartridge needs to have a plurality of detection chambers, and support of multiple wavelengths detection and a scan function are needed for an optical detection device which is used to perform measurements in the LOC specimen cartridge.

A related art optical detection device includes a light source unit for scanning a specimen cartridge, and an optical detector for detecting light rays emitted to a detection chamber. In the light source unit, main wavelength light sources having different wavelengths may be arranged, and a sub-wavelength light source is used for correcting an error due to the characteristics of a sample, foreign bodies, and bubbles of the detection chamber. For example, the light source unit of the related art optical detection device includes two main wavelength light sources and one sub-wavelength light source that are arranged on the vertex positions of a triangle, respectively. However, there is a limitation in correcting a measuring error because areas to which light rays are emitted from these light sources vary.

SUMMARY

Exemplary embodiments address at least the above problems and/or disadvantages and other disadvantages not described above. Also, the exemplary embodiments are not required to overcome the disadvantages described above, and may not overcome any of the problems described above.

One or more exemplary embodiments include an optical detection apparatus enabling correction of a measuring error when a scan-type multiple-wavelength optical detection is performed, and a method of compensating a detection error.

According to one or more exemplary embodiments, there is provided an optical detection apparatus for scanning and measuring detection chambers of a specimen cartridge, the apparatus includes a light source unit which has light sources emitting light rays to the detection chambers; and an optical detector which detects light rays emitted to detection chamber, wherein the light sources include: main wavelength light sources which are used for measuring samples of detection chambers; and a sub-wavelength light source which is used for correcting a measuring error, and the main wavelength light sources and the sub-wavelength light source are provided along a scan line in which the detection chambers are scanned.

The main wavelength light sources may be provided in a plurality of lines parallel to the scan line and the sub-wavelength light source may be provided in each of the lines, and a measuring signal detected by light rays emitted from the main wavelength light sources disposed on one line of the plurality of lines may be corrected by a measuring signal detected by a light ray emitted from the sub-wavelength light source disposed on the same line.

The sub-wavelength light source may be disposed between the main wavelength light sources.

The main wavelength light sources and the sub-wavelength light source may be arranged at same intervals.

The specimen cartridge may have a card-type cartridge shape on which the detection chambers are arranged straight in one or more rows, and the main wavelength light sources and the sub-wavelength light source may be arranged along one or more straight lines corresponding to the one or more rows of the detection chambers.

The specimen cartridge may have a disc-type cartridge shape on which the detection chambers are arranged circumferentially in one or more rows, and the main wavelength light sources and the sub-wavelength light source are arranged along one or more arc lines corresponding to the one or more rows of the detection chambers.

The detection chambers of the specimen cartridge may include first detection chambers which are arranged in a first row and second detection chambers which are arranged in a second row, and the light source unit may include a first light source array having first light sources emitting light rays to the first detection chambers, and a second light source array having second light sources emitting light rays to the second detection chambers, and the first light sources may be arranged along a line parallel to a scan line for scanning the first detection chambers, and the second light sources may be arranged along a line parallel to a scan line for scanning the second detection chamber.

When the first light source array is arranged to emit a light ray to the center of one of the first detection chambers of the first row, the second light source array may be arranged to emit a light ray to a position other than the center of one of the second detection chambers of the second row.

Detection of the first detection chambers of the first row and detection of the second detection chambers of the second row may be performed with time intervals.

The band of the main wavelength of the first light source array may be different from the band of the main wavelength of the second light source array.

The optical detector may be provided to face the light source unit with the detection chambers placed between the optical detector and the light source, and measure absorbance of the light rays passing through the detection chambers.

The measuring error may be caused by at least one of the characteristics of a sample, foreign bodies, and bubbles in the detection chamber.

The apparatus may further include a luminous flux limiting unit having an aperture limiting luminous flux of the light rays emitted from the light source unit.

The aperture may be disposed closer to the detection chamber than to the light source unit.

The aperture may have a size smaller than that of any one of detection chambers.

A measuring result of the main wavelength light sources may be corrected by using a measuring result of the sub-wavelength light source on the same position.

The difference between incident positions of the main wavelength light sources and the sub-wavelength light source may be compensated for by giving a time difference to the driving timing of the main wavelength light sources and the sub-wavelength light source.

The wavelength band of the main wavelength light sources may be a band which shows a difference in optical characteristics according to a sample density, and the wavelength band of the sub-wavelength light source may be a band which shows uniform optical characteristics regardless of a sample density.

The wavelength bands of the main wavelength light sources may be different from each other.

The light sources may be pulse-driven, and the optical detector may be synchronized to the pulse driving of the light sources, and in a time-division method, detect light rays emitted to the detection chambers.

The light sources may be light emitting diodes or laser diodes.

The light source unit may further include a monitoring photodiode which performs light quantity monitoring and correction.

According to one or more exemplary embodiments, there is provided a method of correcting a measuring signal for correcting a measuring error of an optical detection apparatus which sequentially scans and measures detection chambers, the method includes: arranging main wavelength light sources which are used for measuring a sample of the detection chamber, and a sub-wavelength light source which is used for correcting a measuring error, on along a scan line in which the detection chambers are scanned; the main wavelength light sources and the sub-wavelength light source emitting light rays to the detection chamber; an optical detector detecting light rays emitted to the detection chambers; and correcting a measuring signal detected by the light rays emitted by the main wavelength light sources, with a measuring signal detected by the light ray emitted from the sub-wavelength light source.

The main wavelength light sources may be disposed on a plurality of lines parallel to the scan line and the sub-wavelength light source is disposed in each of the lines, and a measuring signal detected by the light rays emitted by the main wavelength light sources disposed on one of the plurality of lines may be corrected with a measuring signal detected by the light ray emitted by the sub-wavelength light source disposed on the same line.

The method may further include compensating for the difference between the light incident positions of the main wavelength light sources and the sub-wavelength light source.

The difference between the light incident positions of the main wavelength light sources and the sub-wavelength light source may be compensated for by giving a time difference to the driving timing of the main wavelength light sources and the sub-wavelength light source.

According to the optical detection apparatus and the method of compensating a detection error of the embodiment, light sources of a plurality of wavelengths are disposed in an integrated array, and thus both miniaturization of the light source unit and multiple wavelength inspection are enabled.

According to the optical detection apparatus and the method of compensating a detection error of the embodiment, detection chambers are disposed densely in a two-dimensional (2D) array on a small lap-on-a-cartridge, and thus simultaneous inspection of multiple items is provided.

According to the optical detection apparatus and the method of compensating a detection error of the embodiment, main wavelength light sources and a sub-wavelength light are arranged along a scanning line, and thus accurate correction of error caused by the characteristics of samples, foreign bodies, and bubbles is enabled.

The optical detection apparatus and the method of compensating a detection error according to the embodiment can be used in a small-sized clinical chemical test device capable of supporting simultaneous test of multiple items, miniaturization, and weight lightening, for example, a lab-on-a-chip based POC blood analyzer.

BRIEF DESCRIPTION OF THE DRAWINGS

The above and/or other aspects will become more apparent by describing certain exemplary embodiments with reference to the accompanying drawings, in which.

DETAILED DESCRIPTION

Figure 1:
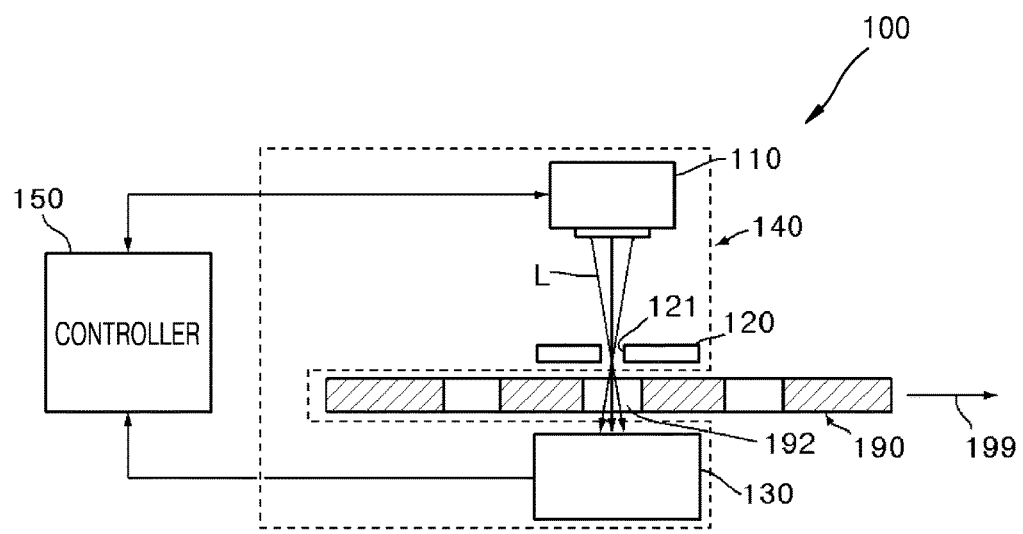
FIG. 1 is a conceptual diagram illustrating a structure of an optical detection apparatus according to an exemplary embodiment.

Certain exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

Expressions such as "at least one of," when preceding a list of elements, modify the entire list of elements and do not modify the individual elements of the list.

Figure 2:
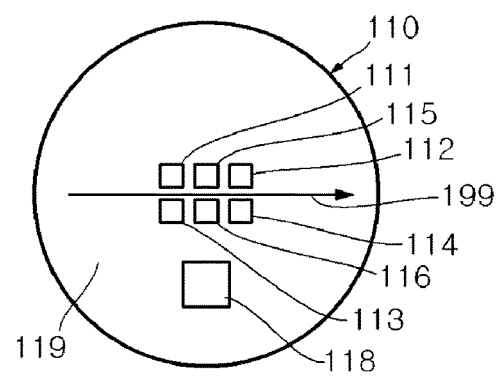
FIG. 2 illustrates a light source unit of the optical detection apparatus of FIG. 1.
Figure 3:
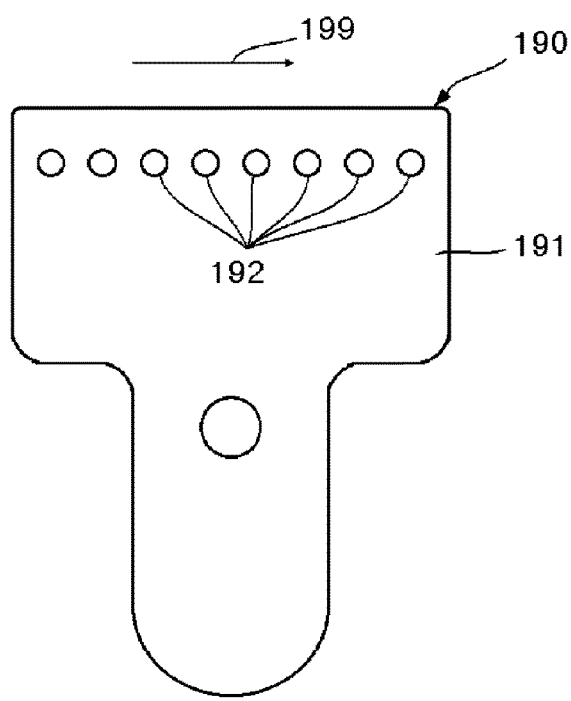
FIG. 3 illustrates a specimen cartridge of the optical detection apparatus of FIG. 1.

FIG. 1 is a conceptual diagram illustrating a structure of an optical detection apparatus 100 according to an exemplary embodiment. FIG. 2 illustrates a light source unit 110 of the optical detection apparatus 100 of FIG. 1. FIG. 3 illustrates a specimen cartridge 190 of the optical detection apparatus 100 of FIG. 1.

Referring to FIG. 1, the optical detection apparatus 100 of the present exemplary embodiment includes a light source unit 110 which emits light rays to a specimen cartridge 190, an optical detector 130 which detects light rays passing through the specimen cartridge 190, and a controller 150 which controls the light source unit 110 and the optical detector 130. The light source unit 110 and the optical detector 130 are provided facing each other, and the specimen cartridge 190 is provided between them. The light source unit 110 and the optical detector 130 move together by a driver (not shown), and thus scan one of detection chambers 192 of the specimen cartridge 190. That is, the light source unit 110 and the optical detector 130 form an optical scanning unit 140 mechanically operating as one body. In another exemplary embodiment, while the light source unit 110 and the optical detector 130 are fixed, the specimen cartridge 190 may move to be scanned.

Referring to FIG. 2, the light source unit 110 emits light rays L to the specimen cartridge 190, and may include a first main wavelength light source through a fourth main wavelength light source 111, 112, 113, and 114, and a first sub-wavelength light source 115 and a second sub-wavelength light source 116. The first and second main wavelength light sources 111 and 112 and the first sub-wavelength light source 115 are arranged as a first row on a straight line along a scan line 199 on a mounting surface 119 of the light source unit 110. The scan line 199 is a line for the light source unit 110 to scan the specimen cartridge 190, and may be a straight line. The first sub-wavelength light source 115 may be disposed between the first and second main wavelength light sources 111 and 112. The first and second main wavelength light sources 111 and 112 and the first sub-wavelength light source 115 may be arranged on the first row at same intervals. The third and fourth main wavelength light sources 113 and 114 and the second sub-wavelength light source 116 are arranged as a second row on a straight line along the scan line 199 on the mounting surface 119 of the light source unit 110, and the second sub-wavelength light source 116 may be disposed between the third and fourth main wavelength light sources 113 and 114. The third and fourth main wavelength light sources 113 and 114 and the second sub-wavelength light 116 may be arranged on the second row at same intervals. The first row on which the first and second main wavelength light sources 111 and 112 and the first sub-wavelength light source 115 are disposed and the second row on which the third and fourth main wavelength light sources 113 and 114 and the second sub-wavelength light source 116 are disposed are parallel to each other. In FIG. 2, a structure in which the first through fourth main wavelength light sources 111 through 114 and the first and second sub-wavelength light sources 115 and 116 are arranged in two rows and three columns is shown, but an exemplary embodiment is not limited thereto. The first through fourth main wavelength light sources 111 through 114 and the first and second sub-wavelength light sources 115 and 116 may be arranged in two rows in a series of zigzags.

As the first through fourth main wavelength light sources 111 through 114 and the first and second sub-wavelength light sources 115 and 116, a combination of a light source having a wide bandwidth and a band pass optical filter passing only light rays in predetermined wavelength bands may be used. Instead of the band pass filter, a spectrometer based on an optical grid may be used. As another example, instead of the filter or spectrometer, light sources having a narrow bandwidth emitting a light ray in a predetermined wavelength band may also be used as the first through fourth main wavelength light sources 111 through 114 and the first and second sub-wavelength light sources 115 and 116. For example, the first through fourth main wavelength light sources 111 through 114 and the first and second sub-wavelength light sources 115 and 116 may be light emitting diodes (LEDs) or laser diodes (LDs).

The first through fourth main wavelength light sources 111 through 114 and the first and second sub-wavelength light sources 115 and 116 may be packaged as one module. For example, when the first through fourth main wavelength light sources 111 through 114 and the first and second sub-wavelength light sources 115 and 116 are an LED chip or LD chip, the chips may be packaged in a chip-on-board (COB) or transistor outline (TO) can form, and thus, the light source unit 110 may be formed.

The first through fourth main wavelength light sources 111 through 114 are used to analyze a reagent response of the specimen cartridge 190. For example, the first through fourth main wavelength light sources 111 through 114 may emit light rays in a wavelength band which shows different optical characteristics according to the sample density of the specimen cartridge 190, or which generates an absorbance change according to a reagent response of the specimen cartridge 190. The wavelength bands of the first through fourth main wavelength light sources 111 through 114 are different from each other, and thus a simultaneous test of multiple items is provided by simultaneously measuring optical characteristics of a plurality of wavelengths with respect to a sample placed on the specimen cartridge 190. As another example, all or part of wavelength bands of the first through fourth main wavelength light sources 111 through 114 may be identical.

The first and second sub-wavelength light sources 115 and 116 emit light rays in a wavelength band which shows uniform optical characteristics regardless of the sample density of the specimen cartridge 190, or which does not have any absorbance change by a reagent response of the specimen cartridge 190. The wavelength bands of the first and second sub-wavelength light sources 115 and 116 may be identical to or different from each other. The first sub-wavelength light source 115 is used to correct an error occurring in a measurement result related to the first and second main wavelength light sources 111 and 112 which are in the row to which the first sub-wavelength light source 115 belongs. Likewise, the second sub-wavelength light source 116 is used to correct an error occurring in a measurement result related to the third and fourth main wavelength light sources 113 and 114 which are in the row to which the second sub-wavelength light source 116 belongs.

The light source unit 110 may further include a light quantity detection sensor 118 which monitors light outputs of the first through fourth main wavelength light sources 111 through 114 and the first and second sub-wavelength light source 115 and 116. The light quantity detection sensor may be a photodiode. This light quantity detection sensor 118 may be packaged together when the first through fourth main wavelength light sources 111 through 114 and the first and second sub-wavelength light sources 115 and 116 are packaged as one module.

Referring to FIG. 1 again, the optical detector 130 detects light rays L emitted to the specimen cartridge 190 and may be a light receiving element such as a photodiode or an image sensor.

The optical scanning unit 140 may include a luminous flux limiting unit 120 disposed between the light source unit 110 and the specimen cartridge 190. The luminous flux limiting unit 120 includes one aperture 121. The aperture 121 of the luminous flux limiting unit 120 has a size smaller than that of the detection chamber 192 of the specimen cartridge 190. Also, the aperture 121 of the luminous flux limiting unit 120 may be a pinhole. The aperture 121 of the luminous flux limiting unit 120 may be disposed closer to the specimen cartridge 190 than to the light source unit 110. The luminous flux limiting unit 120 allows light rays L emitted from the first through fourth main wavelength light sources 111 through 114 and the first and second sub-wavelength light sources 115 and 116 of the light source unit 110, to be incident on only one predetermined detection chamber 102 of the specimen cartridge 190. When the aperture 121 of the luminous flux limiting unit 120 is small as a pinhole, light rays L emitted from the light source unit 110 are incident in a separated state, on the detection chamber 192 of the specimen cartridge 190 even without an additional lens.

Referring to FIG. 3, the specimen cartridge 190 may be a lab-on-a-chip in the form of a card-type cartridge in which a plurality of detection chambers 192 are arranged on one side of a flat plate case 191. Specimens, that is, samples, are placed into the detection chambers 192. The plurality of detection chambers 192 may be arranged on a straight line. Also, the specimen cartridge 190 may employ a micro channel unit which keeps a fluid-type specimen in the detection chambers 192 using micro channels. The optical detection apparatus according to the present exemplary embodiment may be used in a variety of fields such as environment monitoring, food inspection, and medical care, and according to the application field, specimens may vary. For example, a specimen may be blood.

In the optical detection apparatus 100 of an exemplary embodiment, while the specimen cartridge 190 is in a fixed state, the light source unit 110 and the optical detector 130 are moved by a driver (not shown) in a direction in which the plurality of detection chambers 192 of the specimen cartridge 190 are arranged, that is, along the scan line 199, and thus the plurality of detection chambers 192 are sequentially scanned. In another example, the light source unit 110 and the optical detector 130 may be in a fixed state, the specimen cartridge 190 moves, and the plurality of detection chambers 192 of the specimen cartridge 190 pass sequentially through an emission area to which the light source unit 110 emits light rays. In either case, the straight line on which the plurality of detection chambers are arranged may be understood as a scan line 199 for scanning the plurality of detection chambers 192 by the light source unit 110.

A method of correcting a measuring error in the optical detection apparatus 100 of the present exemplary embodiment will now be described with reference to FIGS. 4, 5, 6A, and 6B.

Figure 4:
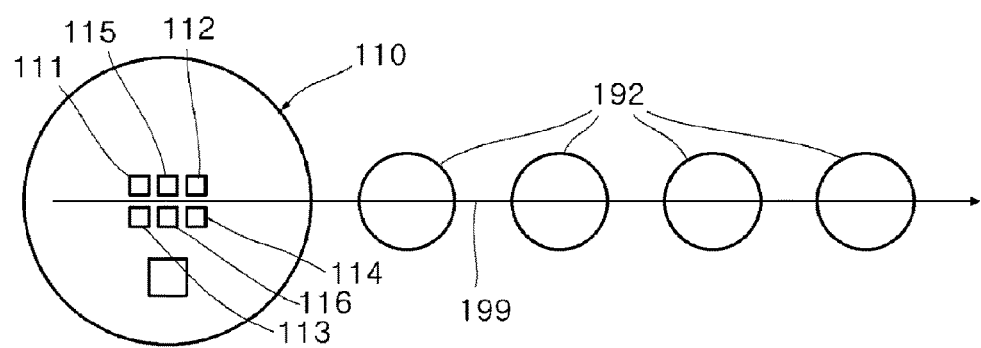
FIG. 4 illustrates the relation between the arrangement of the light source unit and a scan line.
Figure 5:
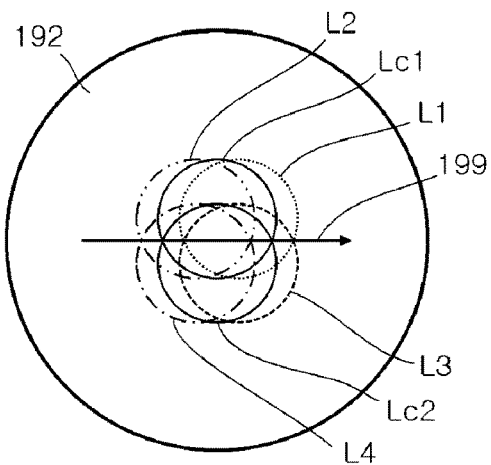
FIG. 5 illustrates beam spots formed on a detection chamber of a specimen cartridge by light rays emitted from the light source unit of FIG. 2.
Figure 6A:
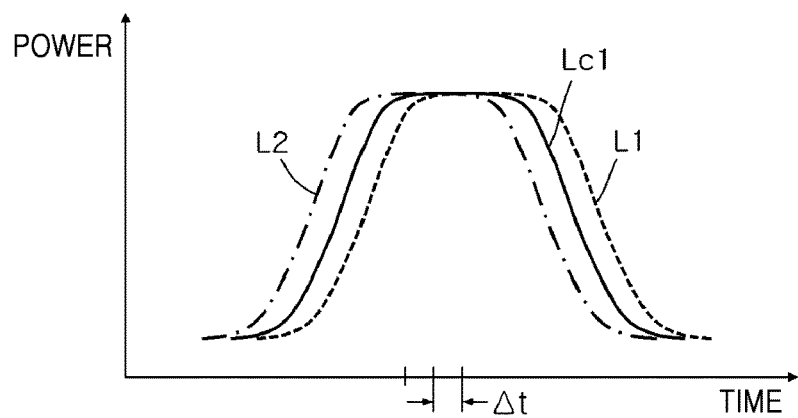
FIGS. 6A and 6B illustrate correction of detection signals by light rays emitted from the light source unit of FIG. 2.
Figure 6B:
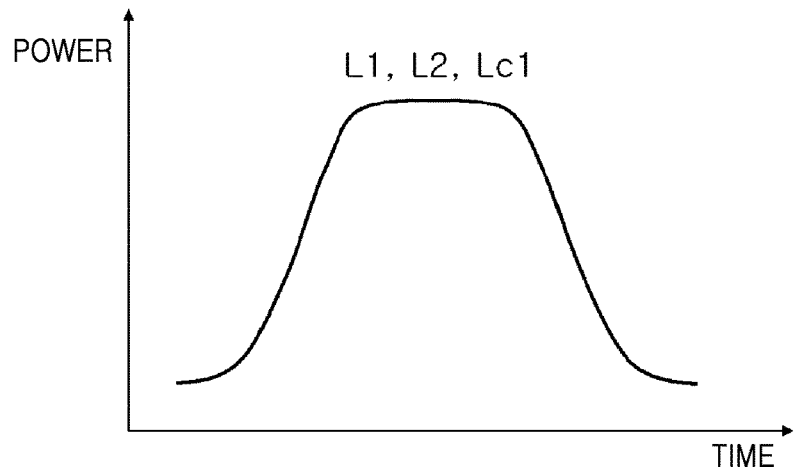
Figure 7A:
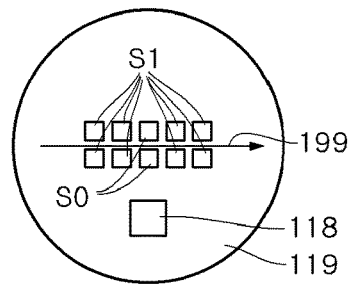
FIGS. 7A, 7B, 7C, and 7D illustrate variation examples of a light source unit employable in the optical detection apparatus of FIG. 1.
Figure 7B:
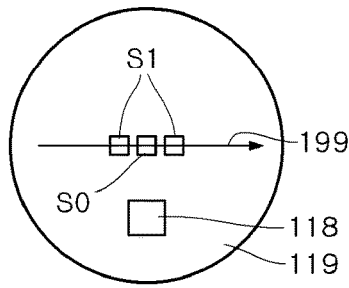
Figure 7C:
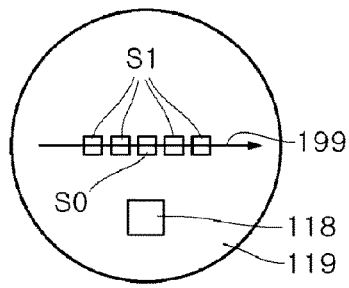
Figure 7D:
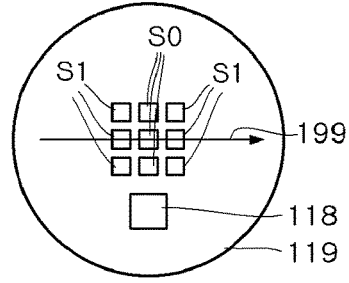

FIG. 4 illustrates the relation between the arrangement of the light source unit 100 and the scan line 199 in the optical detection apparatus 100 of the present exemplary embodiment. FIG. 5 illustrates beam spots formed on the detection chamber 192 of the specimen cartridge 190 when light rays L1, L2, L3, L4, Lc1, and Lc2 are emitted simultaneously from the light source unit 110. FIGS. 6A and 6B illustrate correction of detection signals by light rays emitted from the light source unit 110. Reference numbers L1 through L4, and Lc1 and Lc2 indicate light rays emitted from the first through fourth main wavelength light sources 111 through 114 and the first and second sub-wavelength light sources 115 and 116, respectively.

If the specimen cartridge 190 is inserted into the optical detection apparatus 100, the light source unit 110 is moved in the direction in which the detection chambers 192 of the specimen cartridge 190 are arranged, and is operated to emit light rays L1 through L4 and Lc1 and Lc2. The light rays L1 through L4 and Lc1 and Lc2 emitted from the first through fourth main wavelength light sources 111 through 114 and the sub-wavelength light sources 115 and 116 are incident on a predetermined detection chamber 192 of the specimen cartridge 190 through the aperture 121 of the luminous flux limiting unit 120, and the light rays L1 through L4 and Lc1 and Lc2 passing through the detection chamber 192 are incident on the optical detector 130. As described above, the optical scanning unit 140 (or the specimen cartridge 190) moves along the scan line 199, and thus the plurality of detection chambers 192 of the specimen cartridge 190 are sequentially scanned. The first through fourth main wavelength light sources 111 through 114 and the first and second sub-wavelength light sources 115 and 116 are driven according to pulse signals in a time-division method, and the optical detector 130 performs detections synchronized to the driving pulse. By doing so, the detection signals corresponding to the light rays L1 through L4 and Lc1 and Lc2 can be separated.

If the first through fourth main wavelength light sources 111 through 114 and the first and second sub-wavelength light sources 115 and 116 are simultaneously driven, the light rays L1 through L4 and Lc1 and Lc2 passing through the luminous flux limiting unit 120 of FIG. 1 are emitted to different positions within one detection chamber 192, and thus beam spots are formed, as shown in FIG. 5. Accordingly, before correction by the first and second sub-wavelength light sources 115 and 116, the light incident positions of the light rays L1 through L4 and Lc1 and Lc2 emitted to the detection chamber 192 are compensated.

FIG. 6A shows scan data detected by the optical detector 130 before compensating the light incident positions of the light rays L1, L2 and Lc1 emitted by the first and second main wavelength light source 111 and 112 and the first sub-wavelength light source 115 of the first row. FIG. 6B shows scan data detected by the optical detector 130 after compensating the light incident positions of the light rays L1, L2 and Lc1 emitted by the first and second main wavelength light source 111 and 112 and the first sub-wavelength light source 115 of the first row.

As shown in FIG. 6A, the light rays L1, L2 and Lc1 emitted by the first and second main wavelength light source 111 and 112 and the first sub-wavelength light source 115 of the first row have the light incident positions different from each other, and when the movement of the light source unit 110 is considered, the positional difference on the scan line 199 may be converted into the time difference $\Delta t$. Accordingly, taking the driving time of the first sub-wavelength light source 115 disposed at the center of the first row as a reference, $\Delta t$ is added to the driving time of the first main wavelength light source 111 to make the driving time delayed by Δt, and Δt is subtracted from the driving time of the second main wavelength light source 112 to make the driving time earlier by Δt. By doing so, as shown in FIG. 6B, scan data of the light rays L1, L2, and Lc1 emitted from the first and second main wavelength light sources 111 and 112 and the first sub-wavelength light source 115 can be overlapped accurately on the time axis. Meanwhile, an error caused by the characteristics of a sample, foreign bodies, and bubbles of the detection chamber 192 may occur in a detection signal.

As the first sub-wavelength light source 115 emits a light ray Lc1 in a wavelength band which shows uniform optical characteristics regardless of the sample density of the specimen cartridge 190, or which does not have any absorbance change by a reagent response of the specimen cartridge 190, if the difference between a detection signal by the light rays L1 and L2 of the first and second main wavelength light sources 111 and 112 and a detection signal by the light ray Lc1 of the first sub-wavelength light source 115 is obtained, the error caused by the characteristics of a sample, foreign bodies, and bubbles of the detection chamber 192 may be removed. That is, an offset is given to the driving timing of the first and second main wavelength light sources 111 and 112 and the sub-wavelength light source 115 to compensate the light incident positions, and thus the light rays L1, L2 and Lc1 emitted from the first and second main wavelength light sources and the first sub-wavelength light source 115 of the first row are made to be incident on an identical position on the detection chamber 192. Also, by using the detection signal of the first sub-wavelength light source 115, the error in the detection signals of the first and second main wavelength light sources 111 and 112, caused by the characteristics of a sample, foreign bodies, and bubbles of the detection chamber 192, is compensated for. Likewise, by providing an offset to the driving timing of the third and fourth main wavelength light sources 113 an 114 and the second sub-wavelength light source 116 of the second row, the light incident positions are made to be the same, and by using the second sub-wavelength light source 116, an error in the detection signals of the light rays L3 and L4 emitted from the third and fourth main wavelength light sources 113 and 114 of the second row is compensated for.

In the present exemplary embodiment, an example in which the first and second sub-wavelength light sources 115 and 116 are disposed at the center of the first and second rows, respectively, is described, but an exemplary embodiment is not limited thereto. For example, the first and second sub-wavelength light sources 115 and 116 may be disposed at the front or back of the first and second rows, respectively.

In an exemplary embodiment described above, an example in which light sources of the light source unit 110 are arranged in two rows, and in each row, two main wavelength light sources are arranged is described, but an exemplary embodiment is not limited thereto. FIGS. 7A, 7B, 7C, and 7D illustrate various modified examples of the light source unit 110. As shown in FIGS. 7A through 7D, on the mounting surface 119 of the light source unit 110, main wavelength light sources S1 and sub-wavelength light sources S0 may be arranged in one row or in a plurality of rows along the scan line 199, and in case of the plurality of rows, may be arranged in a 2D matrix. The main wavelength light sources S1 and the sub-wavelength light sources S0 are arranged at same intervals in each row. When the main wavelength light sources S1 and the sub-wavelength light sources S0 are arranged in a plurality of rows, one sub-wavelength light source S0 is disposed in each row. The sub-wavelength light source S0 is disposed at the center of each row, and the main wavelength light sources S1 may be disposed at both sides of the sub-wavelength length light source S0. The sub-wavelength light source S0 may be disposed at a place other than the center of each row. The main wavelength light sources S1 may have all different wavelength bands, or at least a part of the main wavelength light sources S1 may have an identical wavelength band. The number of the main wavelength light sources S1 is not limited in the present exemplary embodiment. Although an example in which one sub-wavelength light source S0 is disposed in each row is described for the present exemplary embodiment, two or more sub-wavelength light sources may be disposed in a row. A light quantity detection sensor 118 for monitoring a light quantity and correction may be further provided.

Figure 8:
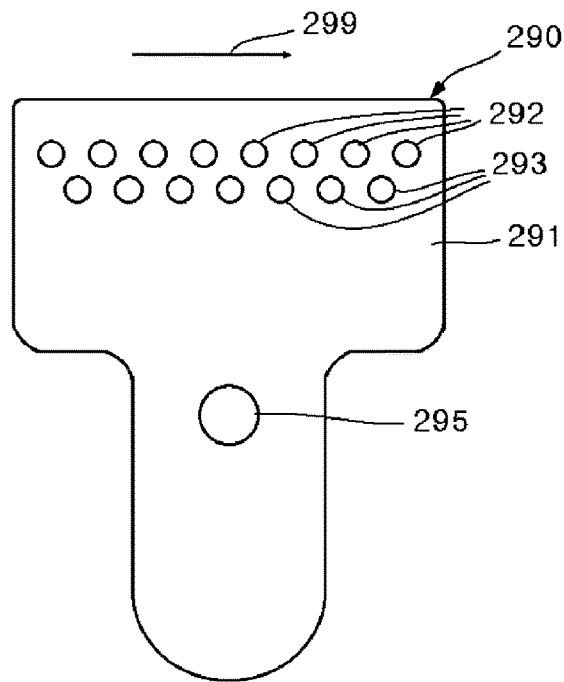
FIG. 8 illustrates a specimen cartridge of an optical detection apparatus according to an exemplary embodiment.
Figure 9:
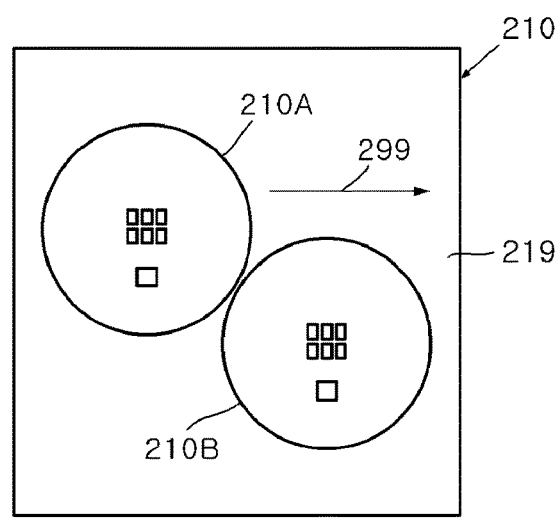
FIG. 9 illustrates a light source unit of the optical detection apparatus, corresponding to the specimen cartridge of FIG. 8.
Figure 10:
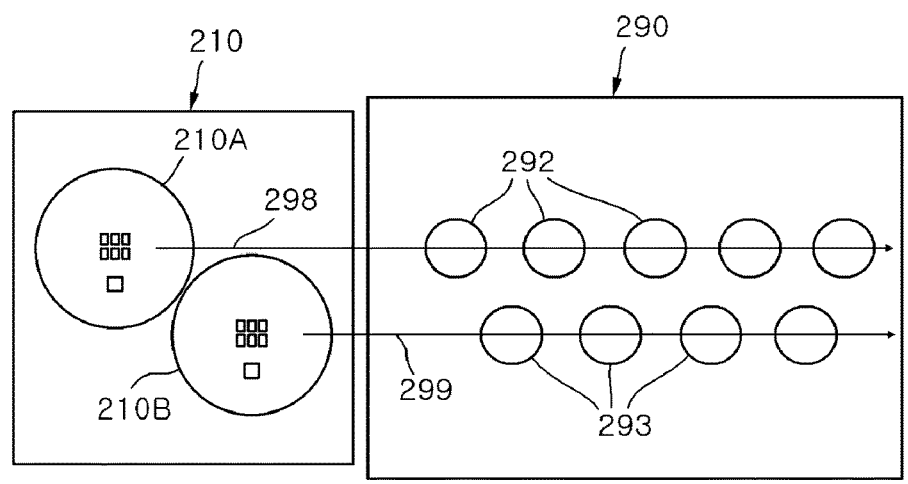
FIG. 10 illustrates the relation between the arrangement of the light source unit and a scan line.

FIG. 8 illustrates a specimen cartridge 290 of an optical detection apparatus according to an exemplary embodiment. FIG. 9 illustrates a light source unit 210 of the optical detection apparatus, corresponding to the specimen cartridge 290 of FIG. 8. FIG. 10 illustrates the relation between the arrangement of the light source unit 210 and a scan line of FIG. 9.

Referring to FIG. 8, the specimen cartridge 290 may be a lab-on-a-chip in the form of a card-type cartridge in which first detection chambers 292 and second detection chambers 293 are arranged in two rows on one side of a flat plate case 291. On the other side of the case 291, an insertion unit 295 into which a specimen is inserted may be provided. The first detection chambers 292 of the first row and the second detection chambers 293 of the second row are arranged on straight lines parallel to each other. The first and second detection chambers 292 and 293 may be disposed at same intervals in respective rows. Furthermore, the first detection chambers 292 of the first row and the second detection chambers 293 of the second row may be arranged in a series of zigzags or in an alternative manner. As described below, the line of the first row of the first detection chambers 292 corresponds to a first scan line 298, and the line of the second row of the second detection chambers 293 corresponds to a second scan line 299.

Referring to FIGS. 9 and 10, the light source unit 210 corresponds to two rows of the first and second detection chambers 292 and 293 of the specimen cartridge 290, and includes a first light source array 210A and a second light source array 210B. Each of the first and second light source arrays 210A and 210B of the light source unit 210 may be the light source unit 110 in the optical detection apparatus described above with reference to FIGS. 1 through 7, or may be variation examples. That is, in each of the first and second light source arrays 210A and 210B, main wavelength light sources are arranged in a row or in a plurality of rows along the first and second scan lines 298 and 299, and one sub-wavelength light source is provided in each row. The main wavelength light sources of the first light source array 210A and the main wavelength light sources of the second light source array 210B may emit light rays in the same wavelength band or different wavelength bands. Each of the first and second light source arrays 210A and 210B may be packaged in a COB, TO can, or other known packaging form.

The first light source array 210A moves along the first scan line 298, and is used for scanning the first detection chambers 292. The second light source array 210B moves along the second scan line 299, and is used for scanning the second detection chambers 293. When the first light source array 210A is arranged to emit light rays to the center of the first detection chambers 292, the second light source array 210B may be arranged to emit light rays to positions other than the center of the second detection chambers 293. In this case, the detection signals of the first detection chambers 292 of the first row and the detection signals of the second detection chambers 293 may be detected with time intervals.

In the optical detection apparatus of the present exemplary embodiment, an optical detector or detectors (not shown) may be further provided for each of the first and second light source arrays 210A and 210B. The optical detection apparatus of the present exemplary embodiment is substantially the same as the optical detection apparatus described above with reference to FIGS. 1 through 7, except that the optical detection apparatus includes the first and second scan lines 298 and 299 corresponding to two rows of the first and second detection chambers 292 and 293 of the specimen cartridge 290. Accordingly, repetitive descriptions will be omitted.

In an example described above with reference to FIGS. 8 through 10, two scan lines are provided, but this is not limiting and three or more scan lines may be provided.

Figure 11:
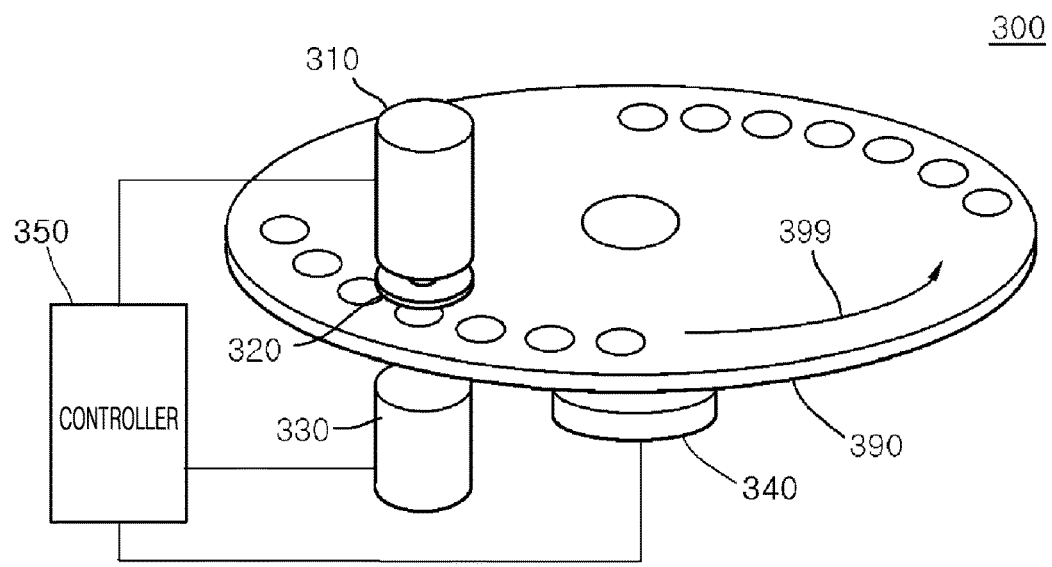
FIG. 11 is a conceptual diagram illustrating an optical detection apparatus according to another exemplary embodiment.
Figure 12:
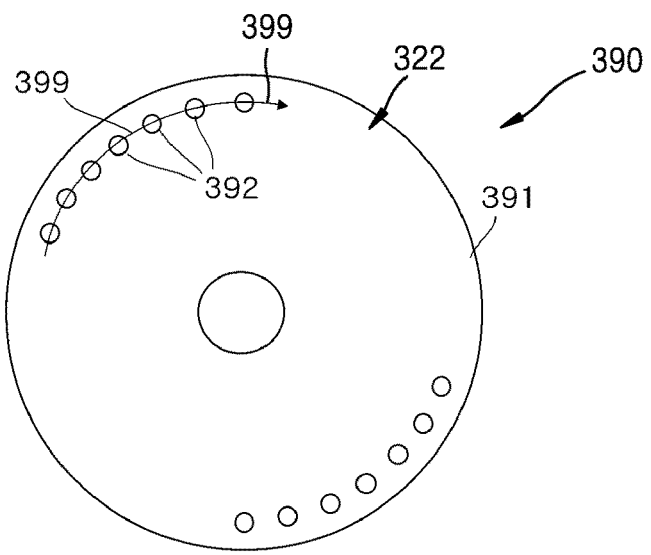
FIG. 12 illustrates a specimen cartridge of the optical detection apparatus of FIG. 11.
Figure 13:
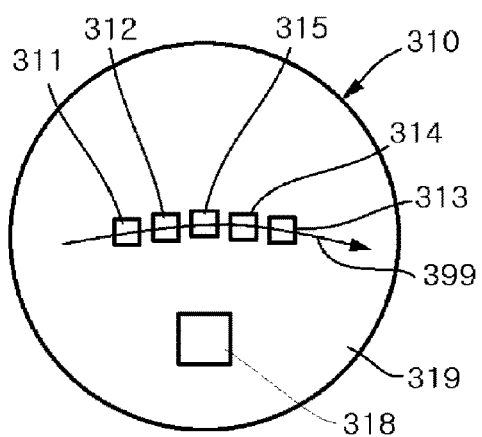
FIG. 13 is a light source unit of the optical detection apparatus of FIG. 11.

FIG. 11 is a conceptual diagram illustrating an optical detection apparatus 300 according to an exemplary embodiment. FIG. 12 illustrates a specimen cartridge 390 of the optical detection apparatus 300 of FIG. 11, and FIG. 13 is a light source unit 310 of the optical detection apparatus 300 of FIG. 11.

Referring to FIG. 11, the optical detection apparatus 300 of the present exemplary embodiment includes a light source unit 310 for scanning light to a specimen cartridge 390, an optical detector 330 for detecting light passing through the specimen cartridge 390, a driver 340 for driving the specimen cartridge 390, and a controller 350 for controlling the optical detector 330 and the driver 340. A luminous flux limiting unit 320 may be additionally provided between the light source unit 310 and the specimen cartridge 390.

The light source unit 310 and the optical detector 330 are arranged to face each other, and the specimen cartridge 390 is inserted between them. The light source unit 310 and the optical detector 330 may be stationary and the specimen cartridge 390 may be rotated and thus, is scanned.

Referring to FIG. 12, the specimen cartridge 390 may be a lab-on-a-CD in a disc-type cartridge shape in which a plurality of detection chambers 392 are arranged on a circumference 322 close to the boundary of a disc-type substrate 391. The specimen cartridge 390 may employ a micro channel unit which keeps a fluid-type specimen in the detection chambers 392 using micro channels. In the detection chambers 392, specimens are placed. In a state in which the specimen cartridge 390 is inserted between the light source unit 310 and the optical detector 330, if the specimen cartridge 390 rotates, the detection chambers 392 of the specimen cartridge 390 pass through between the light source unit 310 and the optical detector 330, and thus are scanned.

Accordingly, the circumference 322 on which the plurality of detection chambers 392 are arranged may be understood as a scan line 399 for the light source unit 310 to scan the plurality of detection chambers 392.

Referring to FIG. 13, the light source unit 310 emits light to the specimen cartridge 390, and may include first through fourth main wavelength light sources 311, 312, 313, and 314, and a sub-wavelength light source 315. The light source unit 310 may further include a light quantity detection sensor 318 for monitoring the light outputs of the first through fourth main wavelength light sources 311 through 314 and the sub-wavelength light source 315. The first through fourth main wavelength light sources 311 through 314 and the sub-wavelength light source 315 are arranged in a row along the scan line 399 on the mounting surface 319 of the light source unit 310. The scan line 399 is a line for the light source unit 310 to scan the specimen cartridge 390, and may be a curved line such as an arc. If the curvature of the scan line 399 is small enough, the scan line 399 may be regarded as a straight line or a substantially straight line. The sub-wavelength light source 315 may be disposed between the first through fourth main wavelength light sources 311 through 314. For example, the sub-wavelength light source 315 may be disposed at the center of the first through fourth main wavelength light sources 311 through 314, that is, between the first and second main wavelength light sources 311 and 312 and the third and fourth main wavelength light sources 313 and 314, but an exemplary embodiment is not limited thereto. The first through fourth main wavelength light sources 311 through 314 and the sub-wavelength light source 315 may be disposed at same intervals along the scan line. The light source unit 310 of the present exemplary embodiment includes the first through fourth main wavelength light sources 311 through 314 and the sub-wavelength light source 315 which are arranged in one row, but the first through fourth main wavelength light sources 311 through 314 and the sub-wavelength light source 315 may be arranged in a plurality of rows.

The first through fourth main wavelength light sources 311 through 314 emit light rays in wavelength bands which generate absorbance changes according to a reagent response of the specimen cartridge 390, and are used to analyze a reagent response of the specimen cartridge 390. The wavelength bands of the first through fourth main wavelength light sources 311 through 314 may be different from each other or at least a part of wavelength bands may be the same. The sub-wavelength light source 315 emits a light ray in a wavelength band which does not have absorbance changes caused by a reagent response of the specimen cartridge 390, and is used to correct an error occurring in a measurement result. As the first through fourth main wavelength light sources 311 through 314 and the sub-wavelength light source 315 are arranged on the same scan line 399, light rays may be made to be incident on an identical position of a predetermined detection chamber 392 of the specimen cartridge 390, by setting a time difference in the driving of the first through fourth main wavelength light sources 311 through 314 and the sub-wavelength light source 315. An error in a detection signal caused by the sample characteristics, foreign bodies, and bubbles on the incident position can be removed by using the sub-wavelength light source 315.

In the present exemplary embodiment, the detection chambers 392 of the specimen cartridge 390 are arranged on one row on a circumference to form one scan line 399, and corresponding to this, the first through fourth main wavelength light sources 311 through 314 and the sub-wavelength light source 315 are arranged on one arc line. However, the present exemplary embodiment is not limited thereto. Similarly to the exemplary embodiment described above with reference to FIGS. 8 through 10, the detection chambers of the specimen cartridge may be arranged in a plurality of rows on the boundary area, to form a plurality of scan lines, and the main wavelength light sources and the sub-wavelength light source may be correspondingly arranged on a plurality of arc lines.

The above-described exemplary embodiments are an example of a method of measuring light rays passing through the detection chambers 192, 292, 293, and 392 of the specimen cartridges 190, 290, and 390. However, exemplary embodiments can be applied identically to a method of measuring light rays reflected on the detection chambers 192, 292, 293, and 392, which can be understood by those skilled in the art.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An optical detection apparatus for scanning detection chambers of a specimen cartridge, the apparatus comprising:
   a light source unit comprising light sources, which emit light rays to the detection chambers, the light sources comprising:
      main wavelength light sources for measuring samples disposed in the detection chambers, the main wavelength light sources emitting the light rays of first wavelength bands being sensitive to an optical response of the samples, and
      a sub-wavelength light source for correcting a measuring error of the main wavelength light sources, the sub-wavelength light source emitting the light rays of a second wavelength band being different from the first wavelength bands and being insensitive to the optical response of the samples, wherein the main wavelength light sources and the sub-wavelength light source are arranged next to one another along a scan line on which the detection chambers are aligned to be scanned;
   a limiting, unit having an aperture which limits luminous flux of the light rays emitted from the main wavelength light sources and the sub-wavelength light source to a certain detection chamber among the detection chambers;
   an optical detector which detects the light rays of the first wavelength bands having been emitted by the main wavelength light sources and passed through the aperture and the certain detection chamber and outputs first measuring signals indicative of characteristics of a certain sample disposed in the certain detection chamber, and additionally detects the light rays of the second wavelength band having been emitted by the sub-wavelength light source and passed through the aperture and the certain detection chamber and outputs a second measuring signal indicative of at least one among foreign bodies and bubbles in the certain sample that cause the measuring error in the first measuring signals; and
   a controller which receives, from the optical detector, the first measuring signals and the second measuring signal, corrects the measuring error in the first measuring signals based on a difference between each of the first measuring signals and the second measuring signal, respectively, and outputs corrected first measuring signals for the certain sample, the measuring error having been removed from the corrected first measuring signals based on the second measuring signal.

2. The apparatus of claim 1, wherein the main wavelength light sources are provided in a plurality of lines parallel to the scan line and the sub-wavelength light source is provided in each of the plurality of lines, and
   the controller is configured to correct the first measuring signals, which are detected based on the light rays emitted from the main wavelength light sources disposed on one line of the plurality of lines, by the second measuring signal detected based on the light rays emitted from the sub-wavelength light source disposed on a same line.

3. The apparatus of claim 1, wherein the sub-wavelength light source is disposed between two of the main wavelength light sources.

4. The apparatus of claim 3, wherein the main wavelength light sources and the sub-wavelength light source are arranged at a same distance from one another.

5. The apparatus of claim 1, wherein the specimen cartridge comprises a card cartridge on which the detection chambers are arranged in one or more rows, and
   the main wavelength light sources and the sub-wavelength light source are arranged along one or more straight lines corresponding to the one or more rows of the detection chambers.

6. The apparatus of claim 1, wherein the specimen cartridge comprises a disc cartridge on which the detection chambers are arranged circumferentially in one or more rows, and
   the main wavelength light sources and the sub-wavelength light source are arranged along one or more arc lines corresponding to the one or more rows of the detection chambers.

7. The apparatus of claim 1, wherein the detection chambers comprise first detection chambers which are arranged in a first row and second detection chambers which are arranged in a second row,
   the sub-wavelength light source includes a first sub-wavelength light source and a second sub-wavelength light source,
   the main wavelength light sources include first main wavelength light sources and second main wavelength light sources,
   the light source unit comprises first light sources having the first main wavelength light sources and the first sub-wavelength light source emitting the light rays to the first detection chambers, and second light sources having the second main wavelength light sources and the second sub-wavelength light source emitting the light rays to the second detection chambers,
   the first light sources are arranged along a line parallel to the scan line for scanning the first detection chambers, and
   the second light sources are arranged along a line parallel to the scan line for scanning the second detection chambers.

8. The apparatus of claim 7, wherein, when the first light sources are configured to emit the light rays to a center of one of the first detection chambers of the first row, the second light sources are configured to emit the light rays to a position other than a center of one of the second detection chambers of the second row.

9. The apparatus of claim 7, wherein the optical detector is configured to detect the light rays from corresponding first detection chambers of the first row and from corresponding second detection chambers of the second row at time intervals.

10. The apparatus of claim 7, wherein a band of the first main wavelength light sources is different from the band of the second main wavelength light sources.

11. The apparatus of claim 1, wherein the optical detector is provided to face the light source unit with the detection chambers placed between the optical detector and the light source unit, and is configured to measure absorbance of the light rays passing through the detection chambers, respectively.

12. The apparatus of claim 1, wherein the aperture is disposed closer to the detection chambers than to the light source unit.

13. The apparatus of claim 1, wherein the aperture has a size smaller than that of any one of the detection chambers.

14. The apparatus of claim 1, wherein the controller controls the main wavelength light sources and the sub-wavelength light source to emit the light rays to a same position on the certain detection chamber.

15. The apparatus of claim 14, wherein the controller is configured to compensate for a difference between light incident positions on the certain detection chamber of the main wavelength light sources and the sub-wavelength light source by providing a time difference between driving times of the main wavelength light sources and the sub-wavelength light source.

16. The apparatus of claim 1, wherein the first wavelength bands of the main wavelength light sources show a difference in optical characteristics according to a sample density, and the second wavelength band of the sub-wavelength light source shows uniform optical characteristics regardless of the sample density.

17. The apparatus of claim 1, wherein the first wavelength bands of the main wavelength light sources are different from each other.

18. The apparatus of claim 1, wherein the light sources are pulse-driven, and the optical detector is synchronized to a pulse driving of the light sources, and, in a time-division method, detects the light rays emitted to the detection chambers, respectively.

19. The apparatus of claim 1, wherein the light sources comprise light emitting diodes or laser diodes.

20. The apparatus of claim 1, wherein the light source unit further comprises a monitoring photodiode configured to perform light quantity monitoring and correction.

21. The apparatus of claim 1, wherein the sub-wavelength light source and the main wavelength light sources are spaced from one another, and emit the light rays to the detection chambers while being moved along the scan line, and the controller controls the main wavelength light sources and the sub-wavelength light source to emit the light rays to a same light incident position on the certain detection chamber, by providing, to the main wavelength light sources and the sub-wavelength light source, a driving signal with a time difference between emission times of each of the main wavelength light sources and of the sub-wavelength list source.

22. The apparatus of claim 21, wherein the controller calculates the corrected first measuring signals based on the second measuring signal that is detected by the optical detector from the same light incident position on the certain detection chamber as that from which the first measuring signals are detected.

* * * * *